US00PP21700P2

(12) United States Plant Patent
Jordan

(10) Patent No.: US PP21,700 P2
(45) Date of Patent: Feb. 8, 2011

(54) ARTICHOKE PLANT 'B13'

(50) Latin Name: ***Cynara scolymus* L.**
Varietal Denomination: B13

(75) Inventor: Stephen Jordan, Lompoc, CA (US)

(73) Assignee: Baroda Farms, Inc., Lompoc, CA (US)

( * ) Notice: Subject to any disclaimer, the term of this patent is extended or adjusted under 35 U.S.C. 154(b) by 0 days.

(21) Appl. No.: 12/587,867

(22) Filed: Oct. 13, 2009

(51) Int. Cl.
*A01H 5/00* (2006.01)

(52) U.S. Cl. ..... Plt./258

(58) Field of Classification Search ..... Plt./258
See application file for complete search history.

(56) References Cited

U.S. PATENT DOCUMENTS

PP16,489 P3 5/2006 Chahbandar

*Primary Examiner*—Annette H Para
(74) *Attorney, Agent, or Firm*—Townsend and Townsend and Crew LLP

(57) ABSTRACT

A new and distinct cultivar of *Cynara* named 'B13' that has improved productivity and year round harvest. B13 produces one central and about fifteen lateral edible immature flower buds, and four side shoots during the first year.

3 Drawing Sheets

Genus and species: The cultivar of this invention is botanically identified as *Cynara scolymus* L.

Variety denomination: The variety denomination is 'B13'.

BACKGROUND OF THE INVENTION

The present invention relates to a new and distinct cultivar of globe artichoke, a perennial herb that is grown as a food crop for the production of edible vegetable delicacies. The new invention is known botanically as *Cynara scolymus* and will be referred to hereinafter by the cultivar name 'B13'. Cynara scolymus is in the family Asteraceae, formerly known as Compositae.

An individual plant of *Cynara scolymus* 'B13' is comprised of main stem, lateral stems, leaves, and immature flower buds known as involucra. Each involucrum is made up of several series of phyllaries also known as involucral bracts. The edible parts of freshly harvested immature flower buds are the fleshy part of the bracts, the fleshy receptacle, and the uppermost part of the peduncle. If not harvested, but permitted to mature, flower buds will develop into flower heads known as capitula.

The new *Cynara* variety named 'B13' was discovered in November 2005 by the inventor as a natural somaclonal variant derived from the parent, an individual *Cynara scolymus*. 'BCP 20-18' (U.S. Plant Pat. No. 16,489). The inventor selected the new variety, now named 'B13', based on the criterion of improved productivity of edible immature flower buds. 'B13' was discovered in and amongst a commercial crop of *Cynara scolymus* 'BCP 20-18' in Lompoc, Calif. At the time of discovery 'B13' was selected as a single plant and segregated and labeled for observation. No chemicals, nor other methods, known to the inventor, were used to induce the new variety 'B13'.

First asexual propagation of 'B13' was conducted by the inventor in April 2006 through the method of crown divisions. Crown divisions then served as explant material for subsequent asexual propagation by tissue culture in July 2006. Under the inventor's supervision, asexual propagation was conducted in Lompoc, Calif. where the plants were labeled and segregated. Since April 2006 under careful observation all plants identified as 'B13' have been determined uniform, stable and true to type in subsequent generations of asexual propagation.

BRIEF SUMMARY OF THE INVENTION

The closest comparison plant is *Cynara scolymus* 'BCP 20-18'. The comparison plant exhibits green flower buds, gray leaves, 1 central flower bud, 4.6 lateral flower buds that are round and slightly open, and 3-4 side shoots during the first year. 'B13' is distinguishable from the comparison plant by greater productivity, number of lateral immature flower buds, number of first year side shoots, glossy leaves, flower bud shape, and flower bud color.

'B13' is characterized by broad spreading habit, yellow-green ribbed stems, yellow-green glossy leaves, 1 central immature flower bud, and 14.9 lateral immature flower buds that are uniform in shape, flavor, and tender consistency. Flower buds are compact globe-shape and yellow-green in color. The edible immature flower buds of 'B13' are harvested year round with greatest productivity during the warm months from March through September. Culture requirements include full sun, well-draining soil, and moderate water. Hardiness is classified as USDA Zone 6.

The following traits have been repeatedly observed and represent the distinguishing characteristics of the new *Cynara* cultivar 'B13'. 'B13' has greatest productivity during the warmer months from March through September. 'B13' exhibits high productivity, producing 1 central and 14.9 lateral immature flower buds as well as 4 side shoots during the first year. Each side shoot of 'B13' produces 1 central and 14.9 lateral immature flower buds per shoot. These traits in combination distinguish 'B13' from all other existing varieties of *Cynara* known to the inventor. 'B13' has not been tested under all possible conditions and phenotypic differences may be observed with variations in environmental, climatic, and cultural conditions, however, without any variance in genotype.

BRIEF DESCRIPTION OF THE DRAWINGS

The accompanying color photographs illustrate the overall appearance of the new *Cynara* cultivar named 'B13'. Photographs were made using conventional techniques and although flower and foliage color may appear different from actual color due to light reflectance, they are as accurate as possible by conventional photography.

Photographs depicted in FIG. 1 and FIG. 2 were taken outdoors in indirect sunlight in April 2009.

Figure 3:
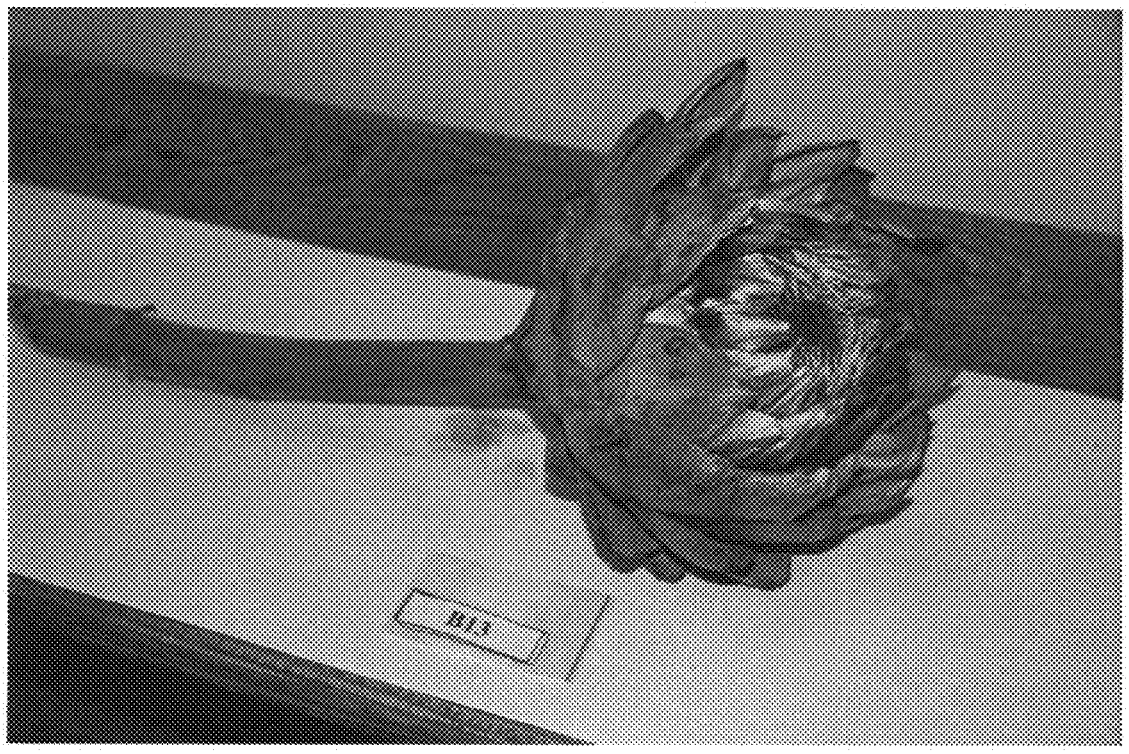

The photograph for FIG. 3 was taken indoors. The photographs are of 10-month-old field grown plants in Lompoc, Calif. Lompoc, Calif. is located on the central coast in Santa Barbara County. Conditions in Lompoc vary with air temperatures ranging from 15.5° Centigrade to 26.6° Centigrade. The relative humidity is generally high. Prevailing winds are northwesterly and rainfall averages twelve inches per year.

Figure 1:
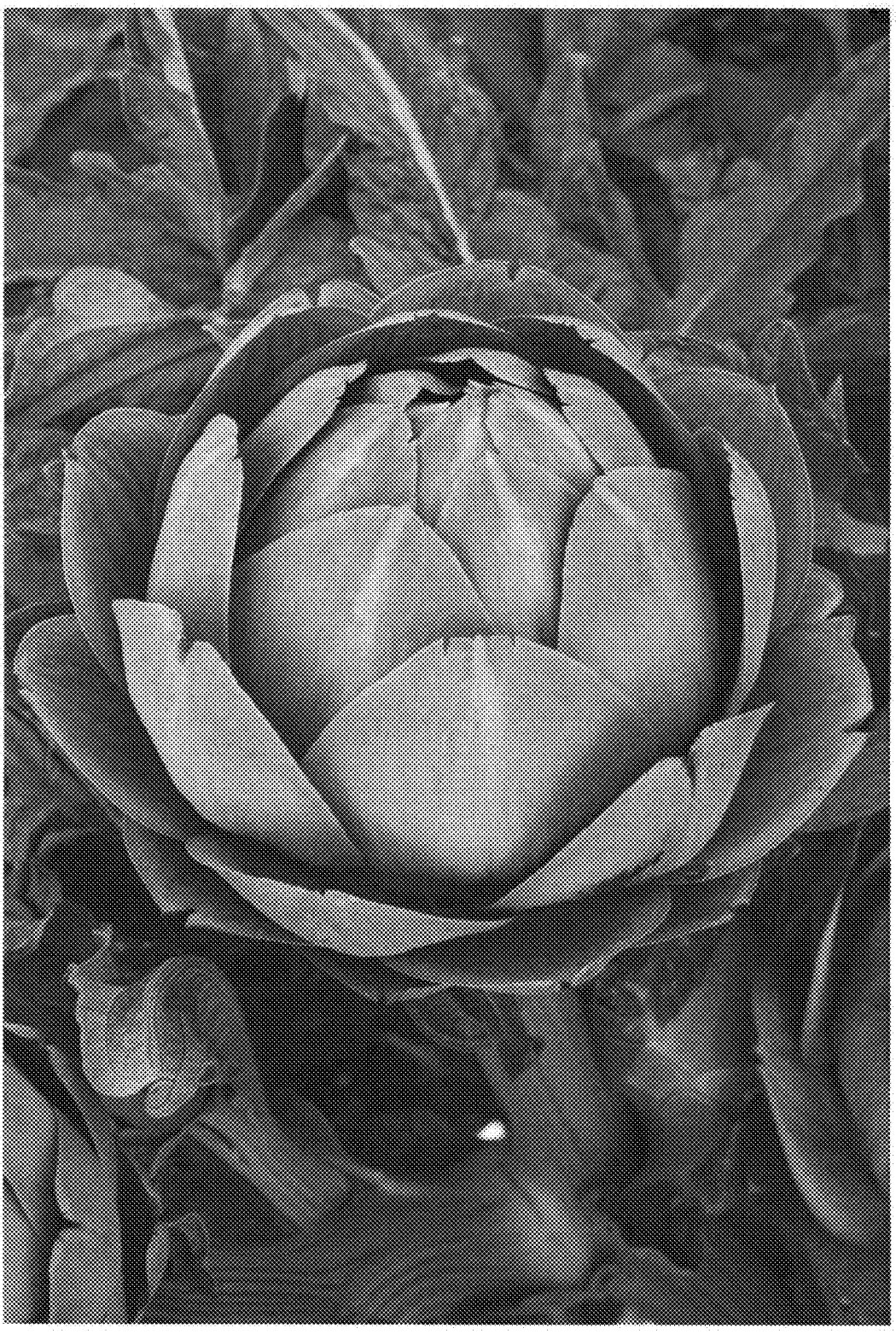

FIG. 1 depicts the central immature flower bud of 'B13'.

Figure 2:
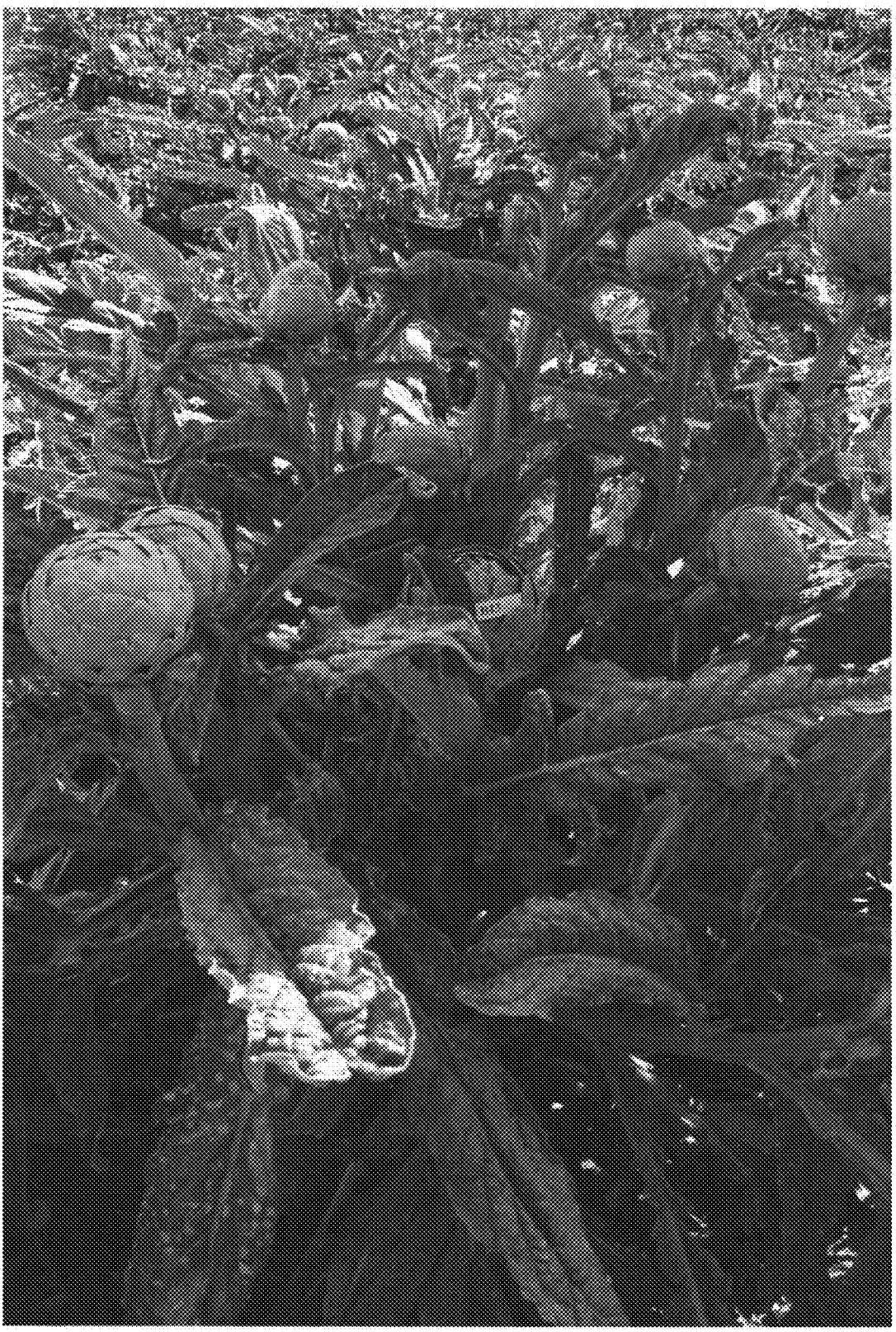

FIG. 2 depicts lateral immature flower buds of 'B13'.

FIG. 3 depicts the mature inflorescence of 'B13'.

BOTANICAL DESCRIPTION OF THE PLANT

The following is a detailed botanical description of the new *Cynara* cultivar named 'B13'. Color determinations are in accordance with The 2001 Royal Horticultural Society Colour Chart of London, England, except where general color terms of ordinary dictionary significance are used. The following observations, measurements and values describe 'B13' as grown in Lompoc, Calif. under conditions used in horticultural practice. The plants were grown in rows where row spacing (bed centers) was at 3 meters and individual plant spacing at 120 cm. Data were collected in April 2009 from 10-month-old field grown plants. Growing requirements are similar to other *Cynara* cultivars.

General characteristics:

- *Months of harvest.*—Year round with greatest productivity during warm months from March through September.
- *Habit.*—Broad spreading.
- *Vigor.*—Vigorous.
- *Type.*—Perennial herb.
- *Height at time of harvest* (*average*).—80 cm.
- *Width at time of harvest* (*average*).—140 cm.
- *Root system.*—Thick and fibrous.
- *Hardiness.*—USDA Zone 6.
- *Propagation method.*—Tissue culture and division.
- *Crop time* (*range*).—5-6 months to produce a harvestable crop of edible immature flower buds.
- *Disease resistance.*—None known to the inventor.
- *Pest and disease susceptibility.*—Aphids, slugs, and leaf spot.
- *Cultural requirements.*—Grow in full sun and well-draining soil, with moderate water.

Stem:

- *Branching habit* (*range*).—Basal to caulescent.
- *Length* (*average*).—28 cm.
- *Diameter* (*average*).—4 cm.
- *Surface.*—A combination of fluted and puberulent.
- *Shape.*—Columnar.
- *Strength.*—Rigid.
- *Color.*—146B.
- *Side shoots* (*average*).—4 during first year.
- *Internode* (*average*).—7 cm.

Foliage:

- *Type.*—Evergreen.
- *Arrangement.*—Spiral.
- *Division.*—Simple.
- *Margin* (*range*).—Laciniate to incised.
- *Quantity* (*range*).—37-45 leaves per individual plant.
- *Shape.*—Pinnatifid.
- *Attachment.*—Decurrent.
- *Leaf color* (*abaxial surface*).—147A.
- *Leaf color* (*adaxial surface*).—194A.
- *Length* (*range*).—40-99 cm.
- *Width* (*range*).—18-20 cm.
- *Apex* (*range*).—Emarginate to acute.
- *Base.*—Truncate.
- *Lobe quantity* (*average*).—12 lobes per leaf.
- *Lobe apex.*—Rounded.
- *Lobe length* (*average*).—9 cm.
- *Lobe width* (*average*).—3.50 cm.
- *Venation pattern.*—Reticulate.
- *Vein color* (*abaxial surface*).—191B.
- *Vein color* (*adaxial surface*).—194A.
- *Surface* (*abaxial*).—Tomentose.
- *Surface* (*adaxial*).—Pubescent.
- *Abaxial surface appearance.*—Matte.
- *Adaxial surface appearance* (*range*).—Glossy to semi-glossy.
- *Stipules.*—None observed.
- *Fragrance.*—None observed.
- *Angle of leaf to stem* (*average*).—45°.

Involucrum (immature flower bud):

- *Shape.*—Globose.
- *Apex.*—Obtuse.
- *Base.*—Rounded.
- *Bud depth* (*range*).—8-16 cm.
- *Bud diameter* (*range*).—8-16 cm.
- *Form.*—Compact.
- *Texture.*—Firm.
- *Surface.*—Glabrous.
- *Quantity* (*average*).—1 central and 14.9 lateral.
- *Phyllary* (*involucral bract*).—Arrangement: Imbricate. Outer bract quantity (average): 50 per involucrum. Inner bract quantity (average): 50 per involucrum. Outer bract shape: Ovate. Inner bract shape: Spathiform. Margin: Entire. Outer bract texture: Fleshy. Inner bract texture: Papyraceous. Outer and inner bract height (average): 7.50 cm. Outer and inner bract width (average): 7 cm. Outer and inner bract surface (abaxial): Glabrous. Outer and inner bract surface (adaxial): Glabrous. Outer and inner bract color (abaxial surface): 146D. Outer and inner bract color (adaxial surface): 146D. Outer bract appearance: Matte. Inner bract appearance: Irridescent. Apex (range): Subacute to retuse with spine. Base: Truncate. Spine color: N199C. Spine dimensions (average): 2 mm. in height and 1.50 mm. in width.
- *Receptacle shape.*—Slightly concave.
- *Receptacle diameter* (*average*).—10 cm.
- *Receptacle depth* (*range*).—2.50-3 cm.
- *Receptacle color:* 155C.
- *Receptacle texture.*—Firm.
- *Bristle color.*—155D.
- *Bristle quantity.*—200+.
- *Bristle shape.*—Filamentous.

*Bristle length* (*average*).—5 cm.
*Bristle width* (*average*).—<1 mm.
*Bristle texture.*—Sericeous.
*Peduncle shape.*—Columnar.
*Peduncle length* (*average*).—20 cm.
*Peduncle diameter* (*average*).—3 cm.
*Peduncle color.*—Individual colors 147B.
*Peduncle strength.*—Rigid.
*Peduncle surface.*—A combination of ribbed and tomentose.
*Duration of cold storage* (*range*).—22-24 days.
*Cold storage temperature* (*range*).—1° -2° Centigrade.
*Cold storage response.*—Negligible browning and softening at stem cut.
*Shelf life* (*range*).—22-28 days under mist.
*Weight* (*average*).—603.1 grams.

Mature inflorescence:
*Type.*—Capitula.
*Persistent or self-cleaning.*—Persistent.
*Shape.*—Oblate.
*Appearance.*—Thistle-like.
*Depth* (*average*).—17 cm.
*Diameter* (*average*).—27 cm.
*Phyllary* (*involucral bract*).—Arrangement: Imbricate. Outer bract quantity (average): 54 in number. Inner bract quantity (average): 65 in number. Outer bract shape: Ovate. Inner bract shape: Spathiform. Outer and inner margin: Entire. Outer bract texture: Fleshy. Inner bract texture: Papyraceous. Outer bract height (average): 8.50 cm.

Inner bract height (average): 9.50 cm. Outer bract width (average): 7 cm. Inner bract width (average): 4 cm. Outer and inner bract surface (abaxial): Glabrous. Outer and inner bract surface (adaxial): Glabrous. Outer bract color (abaxial surface): 144A. Outer bract color (adaxial surface): 144A. Inner bract color (abaxial surface): N199D. Inner bract color (adaxial surface): N199D. Outer bract appearance: Matte. Inner bract appearance: Irridescent. Outer bract apex: Spinescent. Inner bract apex: Emarginate with spine. Base (outer and inner bracts): Truncate. Spine color (inner bract): N199D. Spine dimensions (average): <1 mm. in height and <1 mm. in width.

*Receptacle shape.*—Concave.
*Receptacle diameter* (*average*).—14 cm.
*Receptacle depth* (*average*).—4 cm.
*Receptacle color.*—155C.
*Receptacle texture.*—Firm.
*Disc floret quantity* (*average*).—300+.
*Corolla dimensions* (*average*).—7.25 cm. in depth and 0.25 cm. in width.
*Corolla shape.*—Tubular.
*Corolla color.*—86B.
*Corolla lobe.*—8 in number.
*Lobes fused or unfused.*—Fused.
*Pappus* (*modified calyx*).—Present. Pappus dimensions (average per floret): 5 cm. in length and 1 cm. in width. Pappus appearance: Irridescent. Pappus texture: Sericeous. Pappus color: 159D. Bristle quantity (average): 25 per disc floret. Bristle shape: Filamentous. Bristle color: 159D.
*Peduncle dimensions* (*range*).—44-54 cm. in length and 1.50-1.75 cm. in width.
*Peduncle surface.*—A combination of deeply fluted and tomentose.
*Peduncle color.*—147B.
*Fragrance.*—Tangy.
*Weight* (*average*).—1360 grams.
*Lastingness of inflorescence* (*range*).—2-3 weeks.

Reproductive organs:
*Stamen.*—8 epipetalous stamens.
*Stamen length* (*average*).—1.50 cm.
*Stamen color.*—86B.
*Anther.*—8 connate to stamen.
*Anther length.*—5 mm.
*Anther color.*—86B.
*Style branches.*—2 in number.
*Style branch length.*—0.75 cm.
*Style branch color.*—91A.
*Style color.*—91D.
*Style length.*—2 cm.
*Ovary position.*—Inferior.
*Ovary shape.*—Oblong.
*Ovary dimensions.*—0.60 cm. in height and 0.30 cm. in width.
*Ovary color.*—159A.

Seed: None observed to date.

What is claimed is:

1. A new and distinct variety of artichoke plant having the characteristics substantially as described and illustrated herein.

* * * * *